US00PP37518P2

(12) United States Plant Patent
Assaf

(10) Patent No.: US PP37,518 P2
(45) Date of Patent: Jul. 7, 2026

(54) ***CANNA* PLANT NAMED 'SAACAN01'**

(50) Latin Name: *Canna hybrida*
Varietal Denomination: SAACAN01

(71) Applicant: Azriel Assaf, Kibbutz Saad (IL)

(72) Inventor: Azriel Assaf, Kibbutz Saad (IL)

( * ) Notice: Subject to any disclaimer, the term of this patent is extended or adjusted under 35 U.S.C. 154(b) by 0 days.

(21) Appl. No.: 19/339,045

(22) Filed: Sep. 24, 2025

(51) Int. Cl.
*A01H 5/02* (2018.01)
*A01H 6/00* (2018.01)

(52) U.S. Cl.
USPC ..... Plt./415

(58) Field of Classification Search
USPC ..... Plt./415
See application file for complete search history.

(56) References Cited

U.S. PATENT DOCUMENTS

PP13,809 P3 * 5/2003 MacCormick ..... A01H 5/02
Plt./415

* cited by examiner

*Primary Examiner* — Susan Mccormick Ewoldt

(57) ABSTRACT

A new and distinct cultivar of *Canna* plant named 'SaaCan01' is disclosed, characterized by colorful striped foliage and a red flower. The new cultivar is a *Canna*, typically produced as an outdoor ornamental plant.

1 Drawing Sheet

Latin name of the genus and species: *Canna hybrida*.
Cultivar denomination: 'SAACAN01'.

BACKGROUND OF THE INVENTION

The new cultivar is a product of chance discovery. The new cultivar was discovered by the inventor as a whole plant mutation of the cultivar *Canna hybrida* 'Phasion' U.S. Plant Pat. No. 10,569. The discovery was made in the Summer of 2019. 'SAACAN01' was discovered by the inventor at a commercial greenhouse in Kibutz Saad, Israel.

Asexual reproduction of the new cultivar 'SAACAN01' was first performed at the same commercial nursery by vegetative divisions in Fall of 2019. 'SAACAN01' has since produced at multiple generations and has shown that the unique features of this cultivar are stable and reproduced true to type.

SUMMARY OF THE INVENTION

The cultivar 'SAACAN01' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SAACAN01'. These characteristics in combination distinguish 'SAACAN01' as a new and distinct *Canna* cultivar:

1. Unique combination of a red flower color and variegated dark green, greyed-purple and orange striped foliage.

PARENTAL COMPARISON

Plants of the new cultivar 'SAACAN01' are similar to the parent 'Phasion' most horticultural characteristics. However, 'SAACAN01' differs in producing a solid red flower compared to the orange flower of 'Phasion'.

COMMERCIAL COMPARISONS

'SAACAN01' can be compared to the commercial cultivar *Canna* 'MACtro' U.S. Plant Pat. No. 13,809. Plants of 'MACtro' are similar to plants of 'SAACAN01' in most horticultural characteristics, however, 'SAACAN01' differs in the follows:

1. Flower color of the new cultivar is red; flower color of this comparator is yellow and orange.
2. Foliage color of the new cultivar is dark green, greyed-purple and orange; foliage color of this comparator is yellow and green.
3.

'SAACAN01' can also be compared to the unpatented commercial cultivar *Canna* 'Lon01' U.S. Plant Pat. No. 21,350. Plants of 'Lon01' are similar to plants of 'SAACAN01' in most horticultural characteristics, however, 'SAACAN01' differs in the follows:

1. Foliage color of the new cultivar is dark green, greyed-purple and orange; foliage color of this comparator is dark green and bronze.

BRIEF DESCRIPTION OF THE PHOTOGRAPH

The accompanying photograph in illustrates in full color a typical plant of 'SAACAN01' grown outdoors in Israel. This plant is approximately 1 year old, grown in a 1 gallon pot. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'SAACAN01' plants grown outdoors in Israel. Temperatures ranged from about 7° C. to 20° C. at night to 12° C. to 30° C. during the day. No artificial light, photoperiodic treatments or chemical treatments were given to the plants. Measurements and numerical values represent averages of typical plant types.

Botanical classification: *Canna hybrida*. cultivar 'SAACAN01'.

Age of the plant described: Approximately 2 year.

Container size of the plant described: In the ground.

PROPAGATION

Time to initiate roots: About 5 days at temperatures of 25 to 28 degrees C.

Time to develop roots: About 21 days at temperatures of 28 to 31degrees C.

Rhizome description: Near RHS White 155A in color covered with papery scale-like leaves near Brown 200B.

Root description: Thick, fibrous near RHS 158C in color.

PLANT

Growth habit: Upright.

Mature height: 150 cm.

Plant spread: Approximately 50 cm.

Branching characteristics: Non-branching, basal clump forming.

Stem:

*Length*.—Approximately 30 cm.

*Diameter*.—Approximately 1.5 cm.

*Texture*.—Glabrous, slightly ribbed.

*Color*.—Greyed-Purple 183A.

FOLIAGE

Leaf:

*Average length*.—Approximately 30 cm.

*Average width*.—Approximately 15 cm.

*Shape of blade*.—Ovate.

*Apex*.—Acute.

*Base*.—Symmetrical cuneate with sheathing.

*Margin*.—Entire.

*Texture of top surface*.—Smooth to slightly ridged, matte.

*Texture of bottom surface*.—Smooth.

*Quantity of leaves per plant*.—Average range 5 to 10 at one time.

*Color*.—Young foliage upper side: Interveinal zones striped Greyed-Purple 187A. Midrib Orange-Red 34A. Lateral veins Orange 34A. Young foliage under side: Greyed-Purple 187A. Lateral veins 34B and 34C. Midrib 34C. Mature foliage upper side: Interveinal zones striped Yellow-Green 146A, Green NN137A and Greyed-Purple 187A. Midrib Yellow-Orange 20A. Lateral veins Orange 26B. Mature foliage under side: Yellow-Green 147A. Lateral veins 34B and 34C. Midrib 34C.

*Venation*.—Type: Pinnate. Color description above.

Petiole:

*Length*.—Average 10 cm.

*Diameter*.—Average 1 cm.

*Texture*.—Glabrous.

*Color*.—Yellow-Green 147A flushed Greyed-Purple 187A.

Sheath:

*Length*.—Approximately 6.5 cm.

*Width*.—Approximately 1 cm.

*Texture*.—Glabrous.

*Color*.—Greyed-Purple 183A.

FLOWER

Natural flowering season: Spring and Summer.

Inflorescence description: Single flowers arranged on terminal racemes.

Flower longevity on plant: Individual flowers last approximately 2 to 3 weeks.

Quantity of flowers: Approximately 7 to 10 per raceme.

Inflorescence size:

*Height*.—Approximately 30 to 45 cm.

*Diameter*.—Approximately 15 cm.

Inflorescence sheath:

*Length*.—Approximately 10 cm.

*Diameter*.—Approximately 4.5 cm, unrolled, normally very tightly held to stem.

*Texture*.—Inner Surface: Finely ribbed. Outer Surface: Finely ribbed.

*Color*.—Near RHS Yellow-Green 147A with stripes near Greyed-Purple 185A.

Peduncle:

*Length*.—Approximately 50 cm.

*Width*.—Approximately 1.0 cm.

*Color*.—Yellow-Green 147A with stripes near Greyed-Purple 187A.

*Texture*.—Glabrous.

*Strength*.—Very strong.

Flowers:

*Flower form*.—Salverform.

*Flower diameter* (*at widest point*).—7 to 13 cm.

*Flower length* (*height from the base of the pedicel*).—Approximately 10 to 12 cm.

Flower bud: (Just before showing color).

*Length*.—Approximately 5 cm.

*Diameter*.—Approximately 1.5 cm.

*Shape*.—Ovate.

*Color*.—Near RHS Red 44A.

Bracts:

*Quantity*.—Average 3.

*Arrangement*.—Whorled.

*Length*.—Approximately 5 to 6 cm.

*Width*.—Approximately 2.5 to 3.5 cm.

*Shape*.—Elliptic.

*Apex*.—Acute.

*Base*.—Oblique.

*Margin*.—Entire.

*Texture*.—Glabrous.

*Appearance*.—Slightly shiny.

*Color*.—Inner Surface: Green NN137A flushed 187A. Outer surface: Yellow-Green 147A flushed 187A.

Pedicels:

*General description*.—Flattened, nearly fused to peduncle.

*Length*.—Approximately 1 cm.

*Diameter*.—Approximately 5 mm.

*Angle*.—about 45 degrees from Peduncle.

*Strength*.—Very strong.
*Texture*.—Succulent, glabrous
*Color*.—Green NN137A.

Pedicel sheath:
*Texture*.—Chartaceous.
*Length*.—Approximately 2.0 cm.
*Width*.—Approximately 2.1 cm.
*Color*.—Yellow-Green 147A background with striping near Greyed-Purple 187A.

Sepals:
*Quantity*.—3.
*Appearance*.—Matte.
*Length*.—Approximately 4.8 cm.
*Width*.—Approximately 3.3 cm.
*Shape*.—Deltoid.
*Apex*.—Acute.
*Base*.—Cordate.
*Margin*.—Entire.
*Texture*.—Glabrous.
*Color*.—Inner Surface: Red 40B. Outer Surface: Red 40B.

Petals:
*Quantity*.—3.
*Arrangement*.—Whorled.
*Length*.—Approximately 5 cm.
*Width*.—Approximately 3.9 cm.
*Shape*.—Spatulate.
*Apex*.—Obtuse.
*Base*.—Cuneate.
*Margin*.—Entire.
*Texture*.—Inner surface: Glabrous.
*Texture*.—Outer surface: Glabrous.
*Color*.—When opening, inner and outer surfaces: Red 40B. Fully opened, inner surface: Red 40B. Fully opened, outer surface: Red 40B.

Fragrance: Very faint to none.

REPRODUCTIVE ORGANS

Stamens: Quantity 3. 1.8 cm long. Moderate pollen, colored near Yellow 9A.

Gynoecium:

Pistil: 1, approximately 2.5 cm long. Colored Red 40C.
*Ovary color*.—Near RHS Yellow-Green 145B.
*Ovary diameter*.—7 mm.
*Ovary height*.—7 mm.

OTHER CHARACTERISTICS

Seeds: Seed Vessel colored 187B. Infrequent, low production of round, approximately 1 cm diameter seeds near RHS Brown 200B.

Disease/pest resistance: Neither resistance nor susceptibility to common diseases and pets of *Canna* have been observed in the new cultivar.

Temperature tolerance: Tolerates temperatures from approximately 4° C. to 38° C.

What is claimed is:

1. A new and distinct cultivar of *Canna* plant named 'SaaCan01' as herein illustrated and described.

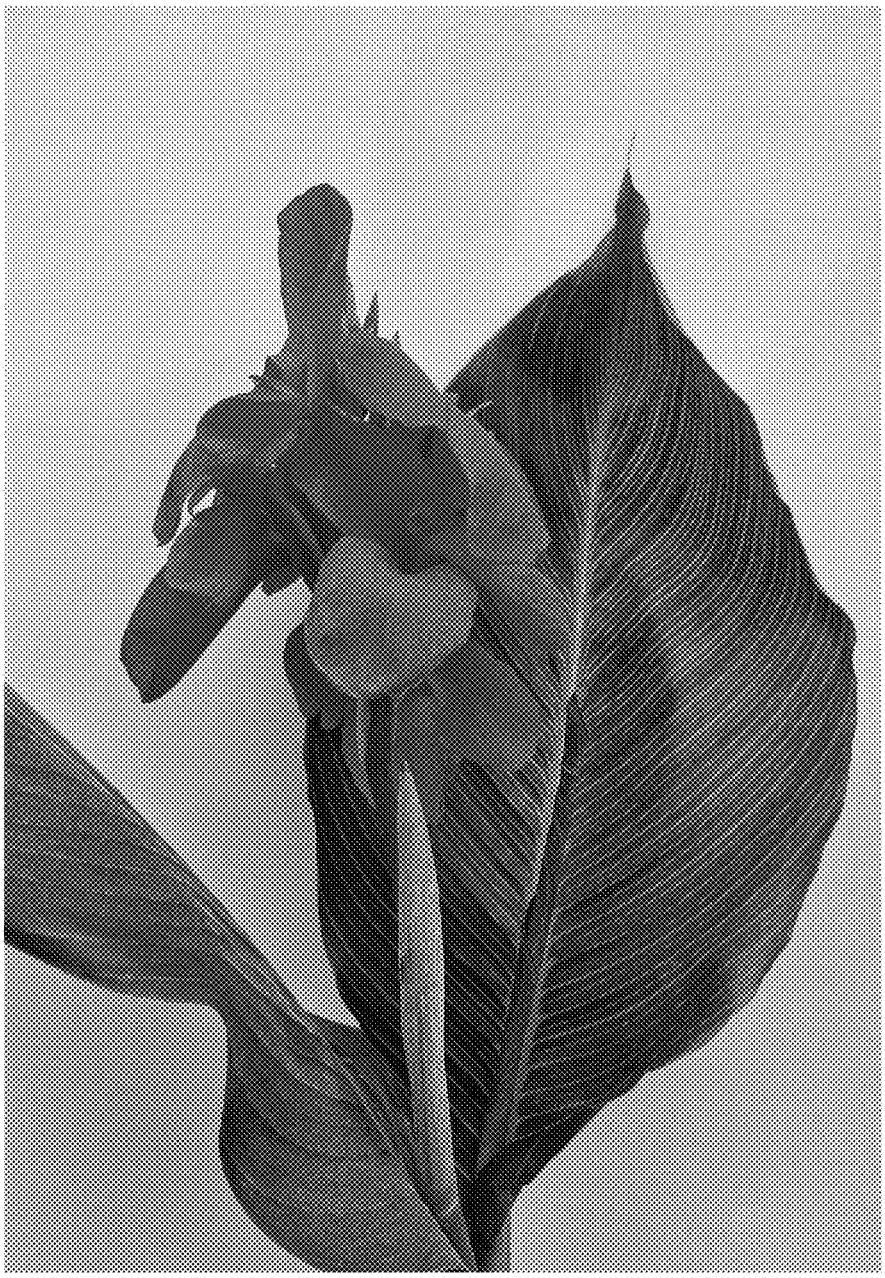

* * * * *